(12) United States Patent
Liemersdorf et al.

(10) Patent No.: US 8,424,366 B2
(45) Date of Patent: Apr. 23, 2013

(54) SEMICONDUCTOR GAS SENSOR HAVING ADDITIONAL FUNCTIONALITIES OF THE SIGNAL-GENERATING ELECTRODE

(75) Inventors: Dirk Liemersdorf, Gerlingen (DE); Richard Fix, Gerlingen (DE)

(73) Assignee: Robert Bosch GmbH, Stuttgart (DE)

( * ) Notice: Subject to any disclaimer, the term of this patent is extended or adjusted under 35 U.S.C. 154(b) by 387 days.

(21) Appl. No.: 12/600,555

(22) PCT Filed: May 16, 2008

(86) PCT No.: PCT/EP2008/056052
§ 371 (c)(1),
(2), (4) Date: Apr. 12, 2010

(87) PCT Pub. No.: WO2009/000598
PCT Pub. Date: Dec. 31, 2008

(65) Prior Publication Data
US 2010/0193375 A1    Aug. 5, 2010

(30) Foreign Application Priority Data

Jun. 25, 2007 (DE) .......................... 10 2007 029 153

(51) Int. Cl.
*G01N 27/407* (2006.01)
(52) U.S. Cl.
USPC .......................................... 73/31.06; 257/253
(58) Field of Classification Search ................... 73/23.2, 73/31.06; 257/253
See application file for complete search history.

(56) References Cited

U.S. PATENT DOCUMENTS 5,698,771 A    12/1997 Shields et al.
2006/0270053 A1   11/2006 Vinayak et al.

FOREIGN PATENT DOCUMENTS

| DE | 19849932 | 5/2000 |
| DE | 102004033597 | 2/2006 |
| EP | 1235070 | 8/2002 |

OTHER PUBLICATIONS

DE 19849932, English Translation of Description accessed on <http://www.epo.org> on May 22, 2012.*
International Search Report, PCT International Patent Application No. PCT/EP2008/056052, dated Sep. 10, 2008.

* cited by examiner

*Primary Examiner* — Lisa Caputo
*Assistant Examiner* — Punam Roy
(74) *Attorney, Agent, or Firm* — Kenyon & Kenyon LLP

(57) ABSTRACT

In a method for operating a semiconductor gas sensor, the gas sensor including at least one gas-sensitive electrode, the method may provide for impression of a voltage sequence on the gas-sensitive electrode. The operation may take place in a measuring cycle which is subdivided into at least one initialization phase and at least one subsequent measuring phase, a first voltage sequence being impressed on the gas-sensitive electrode during the initialization phase, a second voltage sequence being impressed on the gas-sensitive electrode during the measuring phase, and the first voltage sequence differing from the second voltage sequence. A semiconductor gas sensor may be provided for implementing the method according to the invention, and a method may relate to the use of such a sensor.

15 Claims, 3 Drawing Sheets

SEMICONDUCTOR GAS SENSOR HAVING ADDITIONAL FUNCTIONALITIES OF THE SIGNAL-GENERATING ELECTRODE

FIELD OF THE INVENTION

The present invention relates to a method for operating a semiconductor gas sensor, the gas sensor including at least one gas-sensitive electrode, and a voltage sequence being able to be impressed on the gas-sensitive electrode. It also relates to a semiconductor gas sensor for implementing a method as recited in the present invention, and to the use of such a sensor for detecting gases.

BACKGROUND INFORMATION

Using the materials gallium nitride (GaN) and silicon carbide (SiC), it is possible to produce new semiconductor gas sensors for use under extreme environmental conditions. Because of the large band gap of 3.2 to 3.6 eV and the thermal crystal stability, semiconductor components based on these materials are generally suitable for operating temperatures of up to approximately 700° C.

In the case of high-temperature semiconductor gas sensors the gas-sensitive electrode is typically operated at a constant potential. For this purpose, a constant voltage is applied between the gas-sensitive electrode and an electrical connection of the semiconductor structure. In the case of a field-effect transistor as gas sensor, for example, the gate is used as gas-sensitive electrode. This signal-generating gate is connected to a constant potential by applying a constant voltage between gate and source. At the same time, a constant voltage or a constant current is applied between source and drain. If a measurable test gas is then applied to the gate electrode, it causes a change in the voltage or the current between source and drain, which is able to be evaluated as sensor signal.

Semiconductor gas sensors having a gate electrode operated in this manner and suitable electrochemically may be sensitive for nitrogen oxides, hydrocarbons and ammonia. However, at present, additional product-relevant specifications such as selectivity, response and resistance against contamination are not able to be satisfied completely.

U.S. Patent Application Publication No. 2006/0270053 describes a gas sensor having a semiconductor layer, at least one contact being electrically connected to the semiconductor layer. A catalytic gate electrode having a characteristic that changes in the presence of an analyte, as well as a variable bias voltage from a voltage source are provided in addition. The bias voltage may be variable in the sense that it changes over time, e.g., in response to the application of an a.c. bias voltage at the gate contact of the sensor. A bias voltage also may be variable in the sense that a first bias voltage is applied in order to detect a first analyte, while a second bias voltage is applied to the same sensor later on in order to detect a second analyte.

However, in this type of sensor operation, the response time of the sensor until a meaningful sensor signal is obtained depends on how rapidly a steady-state or an otherwise stable state of the reciprocal action of the analyte and the sensor comes about. For some systems this may take longer than would be required to respond to rapidly changing conditions.

SUMMARY OF THE INVENTION

Example embodiments of the present invention provide a semiconductor gas sensor and a method for operating such a semiconductor gas sensor by which the disadvantages of the related art are at least partially able to be overcome.

Accordingly, in an example embodiment of the present invention, a method is provided for operating a semiconductor gas sensor, the gas sensor including at least one gas-sensitive electrode, and a voltage sequence being able to be impressed on the gas-sensitive electrode. In an example, the operation takes place within a measuring cycle, which is subdivided into at least one initialization phase and at least one subsequent measuring phase, a first voltage sequence being impressed on the gas-sensitive electrode during the initialization phase, and a second voltage sequence being impressed on the gas-sensitive electrode during the measuring phase, the first voltage sequence differing from the second voltage sequence.

A semiconductor gas sensor according to the present invention may be designed on the basis of semiconductor materials that are stable under high temperatures. For instance, this may involve a transistor structure or a diode structure. In an example embodiment, a gas-sensitive electrode, which constitutes the signal-generating electrode, is part of the sensor. This signal-generating electrode may be mounted on the semiconductor substrate, or it may be separated from it by a functional layer or a plurality of functional layers. The signal-generating electrode has one or a plurality of electrical contacts. Moreover, this electrode may have catalytic properties. For example, this electrode is able to operate for oxidation or as reducing catalyst. Another option includes the various zones of the electrode exhibiting different catalytic properties.

A voltage sequence within the meaning of the present invention is the characteristic of an electric voltage within a defined time interval, which may be constant as well as variable over time. In the constant case, a d.c. voltage is present. The variable case may be a sine wave, rectangular wave or saw tooth wave having a fixed or variable amplitude, for example. When a voltage sequence is impressed on the gas-sensitive electrode this means that the voltage is applied at this electrode according to the manner provided in the sequence.

A method according to an example embodiment of the present invention takes place in the measuring cycle, which is subdivided into at least one initialization phase and at least one subsequent measuring phase. The measuring cycle may include a continuous repetition, i.e., a repeated run through the initialization phases and the measuring phases. The frequency at which the measuring cycle is repeated may lie within a range from $\geq 0.1$ Hz to $\leq 10$ MHz, more particularly from $\geq 1$ Hz to $\leq 1$ MHz, or more particularly from $\geq 100$ Hz to $\leq 100$ kHz. This takes the speed of the reciprocal action of analyte and gas-sensitive electrode into account so that the information with meaningful measured values is acquired as quickly as possible. In the initialization phase, the gas-sensitive electrode is initialized by impressing a first voltage sequence on the electrode. This creates an initial state at the electrode, which may represent either a steady state such as a chemical equilibrium with regard to the species to be tested on the electrode surface, or a state that is far removed from steady state conditions. For example, the analyte may be absorbed by the electrode surface during the initialization phase. Suitable voltage sequences in the initialization phase include the impression of voltages in the range from $\geq -50$ V to $\leq 50$ V.

In an example, in the measuring phase, a second voltage sequence is impressed. This causes a change in the conditions at the electrode within a very short period of time. The system of analyte-electrode surface must now find a new state, e.g., a state of equilibrium. However, it can follow the switch between initialization and measuring phase only with a certain time delay. The resulting transient sensor signal then allows the analyte concentration to be inferred. The sensor signal utilized for determining the analyte concentration thus comes from the measuring phase. Suitable voltage sequences in the measuring phase include the impression of voltages in the range from $\geq -50$ V to $\leq 50$ V.

The fact that the voltage sequences differ in the initialization phase and the measuring phase means that they differ from each other in at least one characteristic quantity. This may be, for example, the voltage level, the operational sign of the voltage, the frequency or some other time-related differentiation.

A method according to an example of the present invention makes it possible to determine the concentration of an analyte within a short period of time, especially if the a state of equilibrium of the analyte on the electrode surface comes about relatively slowly.

In an example embodiment of the present invention, the method provides that the first voltage sequence and the second voltage sequence correspond to d.c. voltages, and the voltages of the sequences differ in their amount and/or algebraic sign. This means that, overall, a square-wave signal is generated, and the initialization phase of the gas-sensitive electrode falls into the phase of the square-wave signal having a high voltage, and the measuring phase falls into the phase having a lower voltage, for example. However, the situation may also be reversed, i.e., the initialization phase falls into the phase having a lower voltage, and the measuring phase falls into the phase having a high voltage.

In an additional example embodiment of the present invention, the method provides that the first voltage sequence includes a periodically changing voltage, preferably superposed by a voltage that is constant over time. In other words, a sine signal, square-wave signal or saw tooth signal, for example, is generated within the sequence. In order to avoid a phase change of the signal, it is also possible to superpose a constant signal on the periodic signal, so that the algebraic sign of the voltage always remains the same, while the amplitude fluctuates.

In a further example embodiment of the present invention, the method may provide that a lateral electrical field is applied to the gas-sensitive electrode in addition. The gas-sensitive electrode includes at least two physically separated contacts. A potential difference between these contacts results in a lateral electric field and thus in a current flow across the area of the signal-generating electrode. The current flow is a function of the lateral electrode resistance, which may amount to $\geq 10\Omega$ to $\leq 10$ M$\Omega$, for instance. The electric field may be applied in a manner that is constant over time or variable over time. A temporally variable electric field may be synchronized with the initialization and measuring phases according to the present invention. Suitable voltages lie in the range from $\geq -50$ V to $\leq 50$. The field may be applied in a time-variable manner in the form of a sine signal, square-wave signal or saw tooth signal.

The frequency may then lie in a range from $\geq 0.1$ Hz to $\leq 10$ MHz, more particularly from $\geq 1$ Hz to $\leq 1$ MHz or more particularly from $\geq 100$ Hz to $\leq 100$ kHz. The potential may have a linear or non-linear characteristic across the area of the electrode, for instance an exponentially dropping characteristic.

Without a lateral potential gradient, a statistically uniform distribution of the adsorbed gas molecules across the entire electrode surface is to be expected. In contrast, in a potential difference, diverse gas species accumulate across the gas-sensitive electrode either near the positive or near the negative side. Only a portion of the electrode surface is therefore covered. Since particular adsorbed gas molecules lead to a polarization of the electrode near the surface, a sensor signal caused thereby is likewise proportional to the area covered. In this way, a different dependency of the coverage of different gas species from the electrochemical influence allows the development of selectivities.

In addition to a charge transport, a mass transport, e.g., an electro-migration, may be achieved by the potential gradient as well. This makes it possible to directly influence the reaction kinetics of adsorbed gas molecules. Especially the differently expressed effect on different gas species may be utilized for the development of selectivities.

Advantages also result with regard to the expected soot deposition in gas sensors for combustion systems. Without lateral electric fields, the soot particles would distribute on the sensor surface in uniform manner. In contrast, in an advantageous example embodiment, soot first deposits at the poles of the electric fields, i.e., at the edges of the electrode. Only then does a soot bridge form between the poles. A contamination of the gas-sensitive electrode surface is therefore able to be reduced. To remove the soot, the electric field may be deactivated, which causes the soot bridge to collapse and to detach from the electrode. A polarity reversal of the electric field also makes it possible to inhibit or prevent the development of contamination. This applies to the adsorption or desorption of molecules situated on the electrode surface as well.

In a further example embodiment of the present invention, the method provides that the semiconductor gas sensor includes a field-effect transistor, the gas-sensitive electrode representing the gate electrode, and the voltage sequences being applied between the source electrode and gate electrode. Accordingly, the transient characteristic of the source-drain current is used as sensor signal. The effective gate potential is a superpositioning of the source-gate voltage and the additional polarization, which is caused by the adsorbed gas species. The charge exchange curve is therefore also affected by the gas-specific charge transfer. Dynamic electric fields having a suitable time characteristic make it possible to prepare and selectively examine states of non-equilibrium. Another advantage is the possibility of utilizing the different behaviors of different gas species for developing selectivities of the gas sensor.

In addition, it is advantageous if the gate electrode is switched to a load resistance R in the measuring phase. This may be done with the aid of an electronic switch at specific instants, for example in a measuring phase directly following an initialization phase. On the basis of the transient behavior of the charge reversal it is then possible again to determine the concentration of the gas species to be detected. The selectivity may be set via the parameters of the initialization phase. Resistance R may assume values from $\geq 10\Omega$ to $\leq 10$ M$\Omega$, for example. However, it may also assume even higher values. In the case of an infinitely high resistance, a floating gate electrode is involved. In this way, external supplies and discharges of current are minimized during the relaxation period of the chemical equilibrium.

In an example embodiment of the present invention, the method provides that the sensor signals are evaluated by determining the integral of the transient characteristic of the sensor voltage or the sensor current. For this purpose, the individual cycles lasting 0.1 µs, 0.001 ms, 0.01 ms, 0.1 ms, 1 ms, 10 ms or even up to 10 s are separated and the initialization phase is blanked out. If necessary, an offset value is subsequently subtracted from the transient characteristic of the sensor signal in order to correct the sensor signal. The area under the curve characteristic is then calculated by integration.

Example embodiments of the present invention provide a semiconductor gas sensor for implementing a method according to the present invention, which sensor includes a gas-sensitive electrode, a measuring device for measuring the sensor signal, as well as an evaluation device for calculating the concentration of a gas component. The sensor also includes a control device for impressing voltage sequences and/or current sequences on the gas-sensitive electrode.

In an example embodiment of the present invention, the sensor further includes gallium nitride and/or silicon carbide. These semiconductor materials are especially suitable for use as sensor in the exhaust gas of internal combustion engines because they do not lose their stability at the temperatures prevailing in the exhaust gas. In an example embodiment of the present invention, the sensor further includes a field-effect transistor (FET), the gas-sensitive electrode representing the gate electrode, and the voltage sequences and/or current sequences being applied between the source electrode and gate electrode.

Example embodiments of the present invention provide for use of a sensor according to the present invention for the purpose of detecting gases. It may be used in particular as a sensor in the exhaust gas of internal combustion engines, where it detects nitrogen oxides, hydrocarbons, ammonia, $CO_2$ and/or CO. By feeding the measured gas concentrations back to the engine control, it is possible to achieve an engine operation that is adapted to the individual situation.

BRIEF DESCRIPTION OF THE DRAWINGS

The drawings illustrate generally, by way of example, but not by way of limitation, example embodiments of the present invention discussed in detail in the following description.

DETAILED DESCRIPTION

Figure 1:
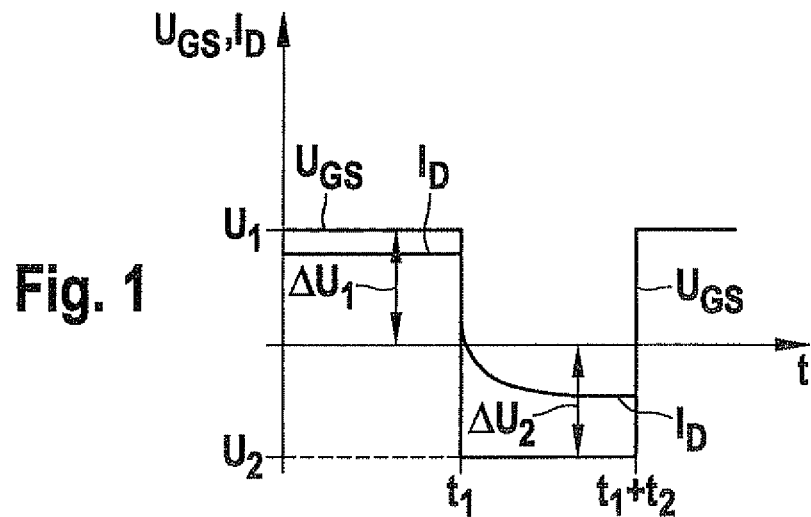
FIG. 1 illustrates a time characteristic of an impressed voltage sequence and a sensor signal according to an example embodiment of the present invention.

FIG. 1 illustrates a time characteristic of an impressed voltage sequence and a sensor signal according to an example embodiment of the present invention. A field-effect transistor is used in the process. The voltage between gate and source $U_{GS}$ is impressed on the gas-sensitive signal-generating electrode, the gate. During the time interval leading up to instant $t_1$, voltage $U_1$ is applied at the gate. Subsequently, for the time interval from $t_1$ to $t_1+t_2$, the voltage applied at the gate is reduced to value $U_2$. The time interval leading up to instant $t_1$ corresponds to the initialization phase, and the time interval from $t_1$ to $t_1+t_2$ corresponds to the measuring phase. The sensor signal, current $I_D$ flowing to the drain, is stable during the initialization phase. Upon the switch to the measuring phase, i.e., when a new state of equilibrium must be adjusted, sensor signal $I_D$ requires some time before reattaining a stable value. The characteristic of the transient curve upon the switch to the measuring phase provides information about the concentration of the gas to be analyzed.

Figure 2:
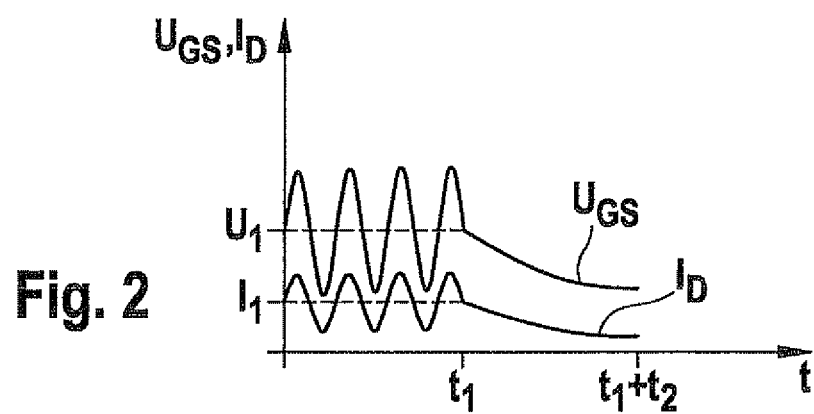
FIG. 2 illustrates a time characteristic of an impressed voltage sequence and a sensor signal according to another example embodiment of the present invention.

FIG. 2 illustrates a time characteristic of the impressed voltage sequence and the sensor signal according to another example embodiment of the present invention. A field-effect transistor is used for this purpose. The voltage between the gate and source $U_{GS}$ is impressed on the gas-sensitive signal-generating electrode, the gate. During the time interval leading up to instant $t_1$, a voltage that is oscillating about the value $U_1$ is applied at the gate. During this initialization phase, sensor signal $I_D$ oscillates about the value $I_1$. In the transition to the measuring phase, i.e., the time interval from $t_1$ to $t_1+t_2$, the impressed voltage no longer oscillates but drops steadily. $I_D$ follows this drop accordingly. The characteristic of the transient curve upon the switch to the measuring phase once again provides the information about the concentration of the gas to be analyzed.

Figure 3:
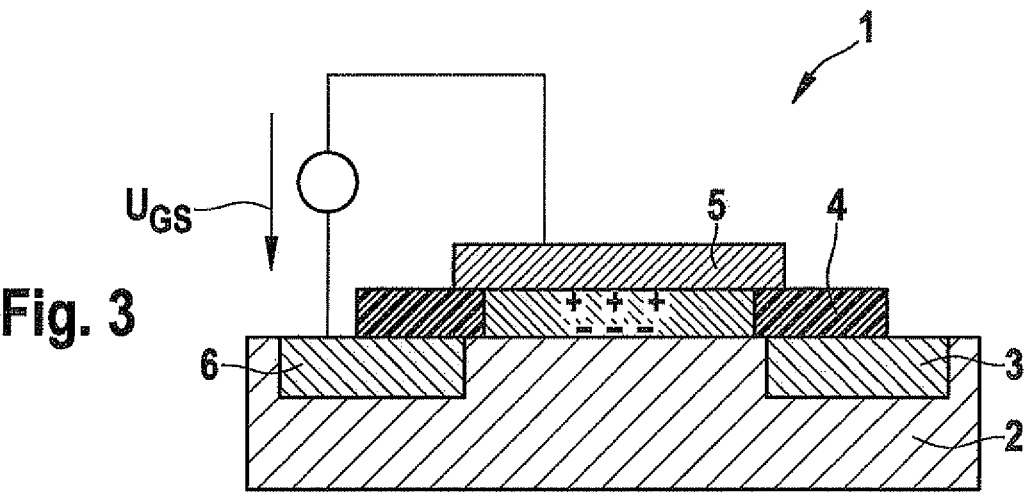
FIG. 3 illustrates a semiconductor gas sensor according to an example embodiment of the present invention.

FIG. 3 shows a semiconductor gas sensor 1 according to an example embodiment of the present invention. A field-effect transistor (FET) is used for this purpose. The transistor includes a semiconductor substrate 2, a drain electrode 3, a dielectric layer 4, a gate electrode 5, and a source electrode 6. The manner in which a voltage $U_{GS}$ is applied between gate 5 and source 6 is shown schematically. This leads to a polarization, which is represented by the symbols +++ and ---.

Figure 4:
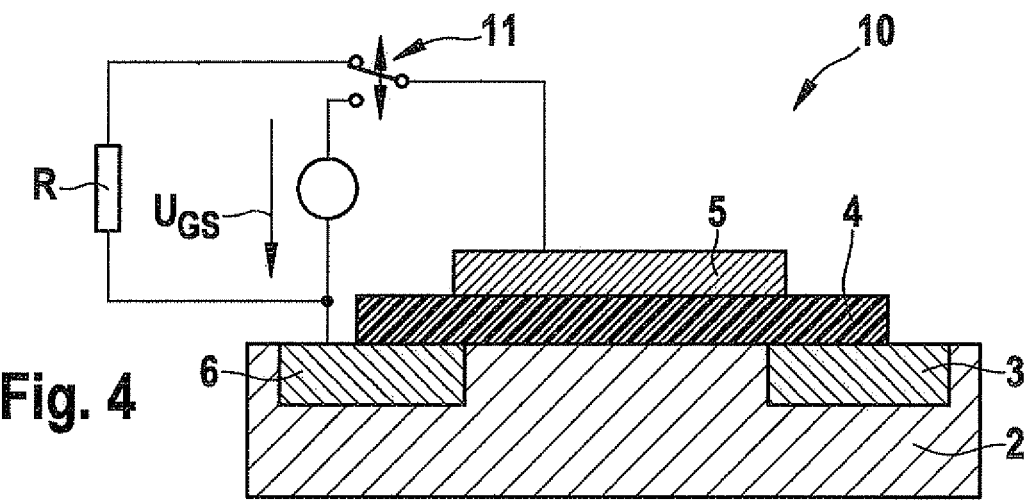
FIG. 4 illustrates a semiconductor gas sensor according to another example embodiment of the present invention.

FIG. 4 shows another semiconductor gas sensor 10 according to another example embodiment of the present invention. A field-effect transistor is used here as well. In contrast to the sensor from FIG. 3, an electronic switch 11 is able to carry out a switch as to whether voltage $U_{GS}$ is applied between gate 5 and source 6 or whether resistance R is switched. If an infinitely high resistance is present, a floating gate electrode is involved. This minimizes external supplies and discharges of current during the measuring phase.

Figure 5:
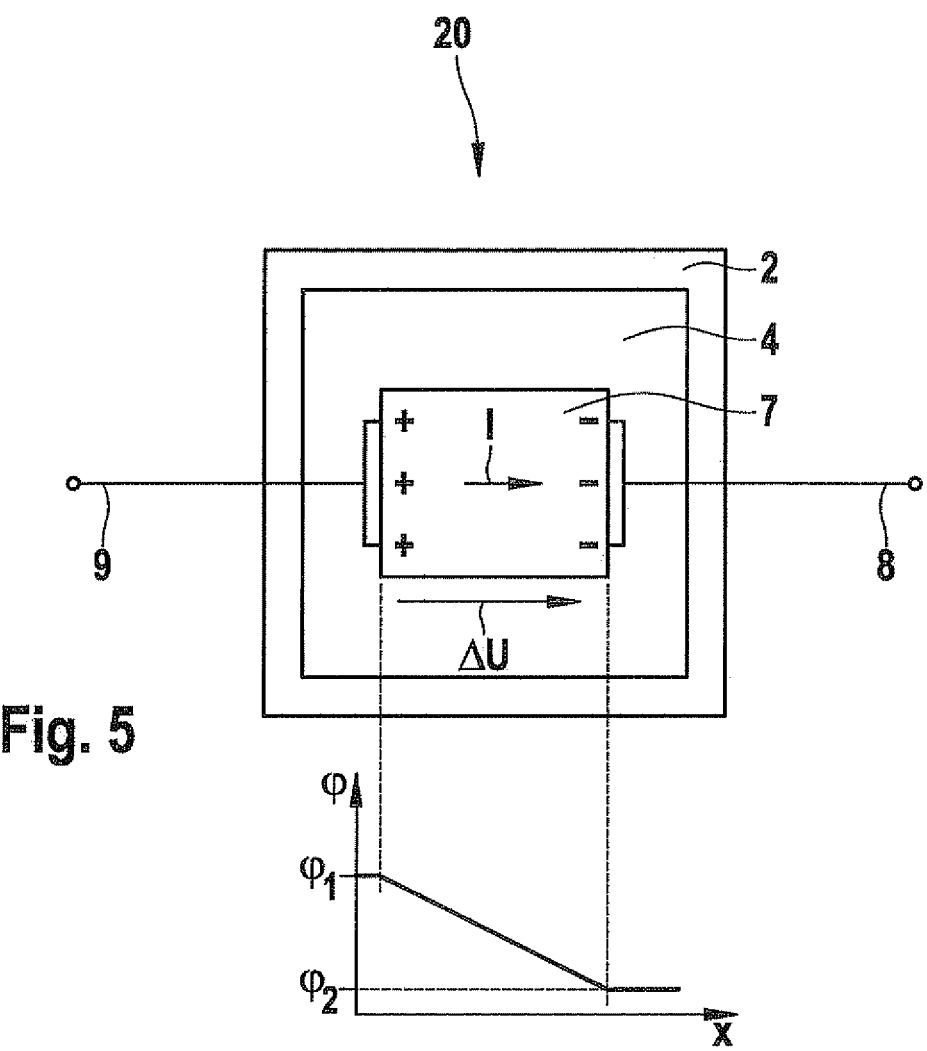
FIG. 5 illustrates application of a lateral electric field to a gas-sensitive electrode according to an example embodiment of the present invention.

FIG. 5 shows the application of a lateral electrical field to the gas-sensitive electrode, according to an example embodiment of the present invention. A sensor unit 20 includes a semiconductor substrate 2 as well as a dielectric layer 4. The signal-generating electrode 7 is connected to electrical contacts 8 and 9. The application of a potential difference between the contacts 8 and 9 polarizes signal-generating electrode 7 in the lateral direction. This is illustrated by the signs +++ and ---. The potential difference and the current flow resulting therefrom are denoted by the symbols I and ΔU. Additionally, the characteristic of the potential across the electrode surface is indicated underneath sensor unit 20. In the x-direction, potential φ continually decreases from a starting potential $\phi_1$ to an end potential $\phi_2$. Highest potential $\phi_1$ is applied at the connection of contact 9 to electrode 7, and lowest potential $\phi_2$ is applied at the connection of contact 8 to the electrode.

What is claimed is:

1. A method for operating a semiconductor gas sensor in a measuring cycle subdivided into at least one initialization phase and at least one subsequent measuring phase, the gas sensor including at least one gas-sensitive electrode, and a voltage sequence being able to be impressed on the at least one gas-sensitive electrode, the method comprising:

impressing a first voltage sequence on the at least one gas-sensitive electrode during the at least one initialization phase;

impressing a second voltage sequence on the at least one gas-sensitive electrode during the at least one measuring phase; and evaluating sensor signals by determining an integral of a transient characteristic of one of a voltage of the sensor and a current of the sensor;
wherein the first voltage sequence differs from the second voltage sequence.

2. The method as recited in claim 1, wherein the first voltage sequence and the second voltage sequence correspond to d.c. voltages, and the sequence voltages differ in at least one of their amounts and their algebraic signs.

3. The method as recited in claim 1, wherein the first voltage sequence represents a periodically varying voltage.

4. The method as recited in claim 1, wherein the first voltage sequence represents a periodically varying voltage superposed by a voltage that is constant over time.

5. The method as recited in claim 1, further comprising:
applying a lateral electric field to the at least one gas-sensitive electrode.

6. The method as recited in claim 1, wherein:
the semiconductor gas sensor includes a field-effect transistor;
the at least one gas-sensitive electrode is a gate electrode; and
the first and second voltage sequences are applied between a source electrode and the gate electrode.

7. The method as recited in claim 6, wherein the gate electrode is switched to a load resistance R in the measuring phase.

8. A semiconductor gas sensor, comprising:
a gas-sensitive electrode;
a measuring device for measuring a signal of the sensor;
an evaluation device for calculating a concentration of a gas component, the evaluation device being configured to evaluate sensor signals by determining an integral of a transient characteristic of one of a voltage of the sensor and a current of the sensor; and
a control device for impressing at least one of voltage sequences and current sequences on the gas-sensitive electrode.

9. The sensor as recited in claim 8, the sensor including gallium nitride and/or silicon carbide.

10. The sensor as recited in claim 8, wherein:
the sensor is operated in measuring cycle subdivided into an initialization phase and a subsequent measuring phase;
a first voltage sequence is impressed on the gas-sensitive electrode during the initialization phase;
a second voltage sequence is impressed on the gas-sensitive electrode during the measuring phase; and
the first voltage sequence differs from the second voltage sequence.

11. The sensor as recited in claim 8, wherein:
the sensor includes a field-effect transistor;
the gas-sensitive electrode is a gate electrode; and
the at least one of voltage sequences and current sequences are applied between a source electrode and the gate electrode.

12. A method, comprising:
detecting gases using a semiconductor gas sensor, wherein the sensor includes:
a gas-sensitive electrode;
a measuring device for measuring a signal of the sensor;
an evaluation device for calculating a concentration of a gas component, the evaluation device being configured to evaluate sensor signals by determining an integral of a transient characteristic of one of a voltage of the sensor and a current of the sensor; and
a control device for impressing at least one of voltage sequences and current sequences on the gas-sensitive electrode.

13. A method for operating a semiconductor gas sensor in a measuring cycle subdivided into at least one initialization phase and at least one subsequent measuring phase, the gas sensor including at least one gas-sensitive electrode, and a voltage sequence being able to be impressed on the at least one gas-sensitive electrode, the method comprising:
impressing a first voltage sequence on the at least one gas-sensitive electrode during the at least one initialization phase; and
impressing a second voltage sequence on the at least one gas-sensitive electrode during the at least one measuring phase;
wherein the first voltage sequence differs from the second voltage sequence;
wherein the first voltage sequence represents a periodically varying voltage superposed by a voltage that is constant over time.

14. A method for operating a semiconductor gas sensor in a measuring cycle subdivided into at least one initialization phase and at least one subsequent measuring phase, the gas sensor including at least one gas-sensitive electrode, and a voltage sequence being able to be impressed on the at least one gas-sensitive electrode, the method comprising:
impressing a first voltage sequence on the at least one gas-sensitive electrode during the at least one initialization phase;
impressing a second voltage sequence on the at least one gas-sensitive electrode during the at least one measuring phase; and
applying a lateral electric field to the at least one gas-sensitive electrode;
wherein the first voltage sequence differs from the second voltage sequence.

15. A method for operating a semiconductor gas sensor in a measuring cycle subdivided into at least one initialization phase and at least one subsequent measuring phase, the gas sensor including at least one gas-sensitive electrode, and a voltage sequence being able to be impressed on the at least one gas-sensitive electrode, the method comprising:
impressing a first voltage sequence on the at least one gas-sensitive electrode during the at least one initialization phase; and
impressing a second voltage sequence on the at least one gas-sensitive electrode during the at least one measuring phase;
wherein the first voltage sequence differs from the second voltage sequence;
wherein the semiconductor gas sensor includes a field-effect transistor, the at least one gas-sensitive electrode is a gate electrode, and the first and second voltage sequences are applied between a source electrode and the gate electrode;
wherein the gate electrode is switched to a load resistance R in the measuring phase.

* * * * *

UNITED STATES PATENT AND TRADEMARK OFFICE
CERTIFICATE OF CORRECTION

PATENT NO. : 8,424,366 B2  Page 1 of 1
APPLICATION NO. : 12/600555
DATED : April 23, 2013
INVENTOR(S) : Liemersdorf et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 491 days.

Signed and Sealed this
Eighth Day of September, 2015

Michelle K. Lee
*Director of the United States Patent and Trademark Office*